(12) United States Patent
Mandhani

(10) Patent No.: US 12,419,777 B2
(45) Date of Patent: Sep. 23, 2025

(54) ERGONOMIC URINE COLLECTING DEVICE

(71) Applicant: Anil Mandhani, Noida (IN)

(72) Inventor: Anil Mandhani, Noida (IN)

( * ) Notice: Subject to any disclaimer, the term of this patent is extended or adjusted under 35 U.S.C. 154(b) by 620 days.

(21) Appl. No.: 17/905,634

(22) PCT Filed: Feb. 22, 2021

(86) PCT No.: PCT/IN2021/050169
§ 371 (c)(1),
(2) Date: Sep. 4, 2022

(87) PCT Pub. No.: WO2021/176463
PCT Pub. Date: Sep. 10, 2021

(65) Prior Publication Data
US 2023/0149203 A1    May 18, 2023

(30) Foreign Application Priority Data
Mar. 5, 2020  (IN) .............................. 202011009393

(51) Int. Cl.
*A61F 5/449* (2006.01)
*A61F 5/44* (2006.01)
*A61F 5/455* (2006.01)

(52) U.S. Cl.
CPC ............ *A61F 5/449* (2013.01); *A61F 5/4405* (2013.01); *A61F 5/455* (2013.01)

(58) Field of Classification Search
CPC ......... A61F 5/449; A61F 5/4405; A61F 5/455
See application file for complete search history.

(56) References Cited

U.S. PATENT DOCUMENTS

| 1,793,737 A | * | 2/1931 | Estes | A41D 13/04 |
| | | | | 2/48 |
| 3,547,123 A | * | 12/1970 | Sachs | A61F 5/453 |
| | | | | 604/350 |
| 4,495,662 A | * | 1/1985 | Miller | A41D 13/1254 |
| | | | | 2/919 |
| 4,511,358 A | * | 4/1985 | Johnson, Jr. | A61F 5/4404 |
| | | | | 604/327 |

(Continued)

FOREIGN PATENT DOCUMENTS

| AU | 2018254610 A1 | 10/2019 |
| WO | 2009035599 A1 | 3/2009 |
| WO | 2019094635 A1 | 5/2019 |

*Primary Examiner* — Guy K Townsend
(74) *Attorney, Agent, or Firm* — Novel Patent Services LLC

(57) ABSTRACT

The present disclosure proposes an ergonomic urine collecting device that provides feeling of passing urine naturally. The ergonomic urine collecting device comprises of a base plate (101), a variable length tube (102), a urine collecting pouch (104), a sensor (not shown), a detachable electronic casing (not shown), and a urine discharge outlet (107). The ergonomic urine collecting device enhances the user comfort and prevents turbulence and bulging of the pouch. The device provides a variable length connector with a one-way valve and the entire equipment fits inside an undergarment. Further, the equipment provides early warning to the user when the content inside the urine collecting pouch reaches a threshold level and aids the user in planning to empty the pouch in time.

10 Claims, 2 Drawing Sheets

(56) References Cited

U.S. PATENT DOCUMENTS

| | | | | |
|---|---|---|---|---|
| 4,606,736 A * | 8/1986 | Van De Weghe | A61F 5/44; 604/327 |
| 5,032,118 A * | 7/1991 | Mason | A61F 5/4408; 604/353 |
| 5,135,519 A * | 8/1992 | Helmer | A61F 5/445; 604/332 |
| 5,142,702 A * | 9/1992 | Piloian | A41D 13/1245; 2/102 |
| 5,935,116 A * | 8/1999 | Kristensen | A61F 5/4408; 2/22 |
| 6,110,156 A * | 8/2000 | Mendonca | A61F 5/445; 604/345 |
| 6,477,710 B1 * | 11/2002 | Ojoyeyi | A41D 13/1236; 2/254 |
| 6,574,800 B1 * | 6/2003 | Leger | A41D 13/1245; 604/174 |
| 6,887,223 B2 * | 5/2005 | Bisbee | A61F 5/453; 224/148.2 |
| 8,486,035 B1 * | 7/2013 | Arce | A61F 5/449; 2/72 |
| D695,893 S * | 12/2013 | Rodsten | D24/122 |
| 9,510,627 B2 * | 12/2016 | Trimble | A41D 13/04 |
| 10,828,210 B1 * | 11/2020 | Chen | A61F 13/84 |
| 11,785,997 B1 * | 10/2023 | Hadfield | A41D 27/20; 2/247 |
| 2007/0225667 A1 | 9/2007 | Otto | |
| 2010/0205720 A1 * | 8/2010 | Ortega Astor | A41D 13/1281; 2/247 |
| 2013/0245584 A1 * | 9/2013 | Krasikoff | A61F 5/4408; 604/327 |
| 2015/0257463 A1 * | 9/2015 | Trimble | A41D 13/04; 2/48 |
| 2020/0064172 A1 | 2/2020 | Tabaczewski et al. | |

\* cited by examiner

ERGONOMIC URINE COLLECTING DEVICE

FIELD OF THE INVENTION

The present disclosure generally relates to the technical field of urostomy bags, and in specific relates to an ergonomic urine collecting device that provides a feeling of passing urine in a natural way, enhances the user comfort and prevents the turbulence and bulging of the pouch.

BACKGROUND OF THE INVENTION

Organ dysfunction or organ failure is a medical condition where a specific organ does not perform its intended function. An organ may fail due to various reasons, the level of organ failure is dependent on the reason for the failure. Organ dysfunction creates the need for medical intervention to carry out homeostasis of the body. Such medical interventions may include acute treatments such as medications or severe treatments including replacement of an organ such as kidney, liver and heart.

The urinary bladder is a muscular sac about the size and shape of a pear. Urine is made in the kidneys and travels down through two tubes called ureters to the bladder. The typical human bladder stores between 300 and 500 ml of urine. The bladder stores urine thereby allowing urination to be infrequent and controlled. When the urinary bladder is removed due to cancer or when the bladder function is affected due to paralysis, surgery is performed to create an alternate passage for the urine using patient's small intestine which is taken out to the surface and called as a stoma. The stoma is then connected to a urine collecting pouch, which requires timely disposal when it is filled.

In general, the urine collection pouch is stuck to the anterior surface of the belly near the belly button and it hangs freely and once it is filled, the patient opens the outlet and empties the pouch at the socially acceptable place where a washbasin is required. Patients lose the feeling of passing urine in stream in standing position. This approach is undesirable because the accumulation of urine in the bag causes bulging of the pouch and movement constantly reminds the presence of the pouch over the belly. Further, the weight of the filled urine pouch results in traction to the stoma plate, to which the pouch is attached and the plate invariably gets loosened up thereby requiring the patient to change the stoma plate frequently. In addition, at night, larger ostomy bags or night bags are typically used. These bags must be hung on wheeled support next to the patient's bed, which interfere with the patient's movements during sleep. There is a need for a device that does not restrict the patient's movements during sleep and further enhances the comfort of the user.

In the updated technology, medical trousers have been used for urine incontinence that includes trousers, a urine mask, and a urine storage bag. The urine mask and the urine storage bag are connected by a catheter. The urine mask is further provided with an elastic band that is bound and fixed with the human body. The trousers provide space for the urine storage bag to thereby enhance the user's decency. However, the user needs to wear the trouser all the time which creates discomfort to the user. There is a need for a device that aids patients with a stoma to discharge urine in a way which looks dignified and close to the act of passing urine naturally.

Therefore, there exists a need for a urine collecting device to facilitate the natural way of urination. There is a need for a device that enhances the user comfort and prevents the turbulence as well as the bulging of the pouch. There exists a need for a urine collecting device that reduces the risk of infection to the user. Such equipment should have the capability to provide early warning to the user when the contents inside the storage bag reach a threshold level. There is a need for a urine collecting device that is socially accepted and restores the dignity of the user.

OBJECTIVES OF THE INVENTION

The primary objective of the invention is to provide an ergonomic urine collecting device to facilitate the natural way of urination (urinating while standing).

The other objective of the invention is to incorporate a variable length connector with a one-way valve in which the entire equipment fits inside an undergarment.

Another objective of the invention is to provide a patterned urine collection pouch that enhances the user comfort and prevents the turbulence as well as the bulging of the pouch.

Further objective of the invention is to reduce the risk of infection to the user by utilizing regulated materials to make the urine collection pouch.

The other objective of the invention is to provide early warning to the user when the contents inside the urine collecting pouch reach a threshold level and aid the user in planning to empty the pouch in time.

Yet another objective of the invention is to provide collecting equipment that is socially accepted and restores the dignity of the user.

SUMMARY OF THE INVENTION

The present disclosure proposes an ergonomic urine collecting device. The following presents a simplified summary in order to provide a basic understanding of some aspects of the claimed subject matter. This summary is not an extensive overview. It is not intended to identify key/critical elements or to delineate the scope of the claimed subject matter. Its sole purpose is to present some concepts in a simplified form as a prelude to the more detailed description that is presented later.

In order to overcome the above deficiencies of the prior art, the present disclosure is to solve the technical problem to provide an ergonomic urine collecting device that provides a natural way of urination, enhances the user comfort and prevents turbulence and bulging of the pouch.

According to an aspect, the invention provides an ergonomic urine collecting device. The ergonomic urine collecting device comprises of a base plate, a variable length tube, a urine collecting pouch, a sensor, a detachable electronic casing, and a urine discharge outlet. The urine collecting device is ergonomically designed which easily fits to the undergarment and facilitates natural way of urination to the patient.

The base plate is configured with an adhesive patch to connect at ostomy site of the patient. The variable length tube connected to the base plate in connection with a non-return valve to provide a channel to the urine released from the ostomy. The non-return valve is positioned at the end of the variable length tube inside the urine collecting pouch to restrict the backflow of urine. The urine collecting pouch is configured with patterns on inner walls of it to collect urine from the variable length tube without turbulence. In specific, the urine collecting pouch is made of medical grade PVC material which is replaceable and detachable. The patterns on the urine collecting pouch are made using sealing that aids to avoid the turbulence of the urine flow and bulging of the urine collecting pouch. In addition, the patterns also attempt to measure volume-based sensing by channelizing the urine.

The sensor is positioned in a pocket chamber which is arranged on the urine collecting pouch at a threshold level to detect and transmit a signal when the fluid inside reaches a threshold limit. The sensor is placed at a threshold level of 350 ml. In specific, the sensor includes either a particle sensor or a capacitive sensor or the like to detect urine level inside the urine collecting pouch. The detachable electronic casing is configured in connection with the sensor to receive the threshold signal and provide haptic feedback to the patient. In specific, the detachable electronic casing comprises a haptic feedback motor, a controller, a power button and a battery, and the controller receives the threshold signal and operates the haptic feedback motor to provide haptic feedback.

The haptic feedback is provided to the patient through shaft-less motor. The haptic feedback motor is a shaft-less motor comprising either a coin motor or an ERM motor or the like. The electronic casing is positioned in contact with the patient's body according to their choice and comprises a charging port to recharge the battery inside it. The detachable electronic casing is detached when the urine collecting pouch is replaced and positioned easily after the replacement. The electronic casing has the flexibility to re-adjust the location to reduce phantom vibration. The urine discharge outlet connected to the end of the urine collecting pouch is configured with a cap to enable the patient to empty the urine collecting pouch after receiving the haptic feedback or when required.

Further, objects and advantages of the present invention will be apparent from a study of the following portion of the specification, the claims, and the attached drawings.

DETAILED DESCRIPTION OF DRAWINGS

The accompanying drawings, which are incorporated in and constitute a part of the specification, illustrate an embodiment of the invention and together with the description, explain the principles of the invention.

DETAILED INVENTION DISCLOSURE

Figure 1:
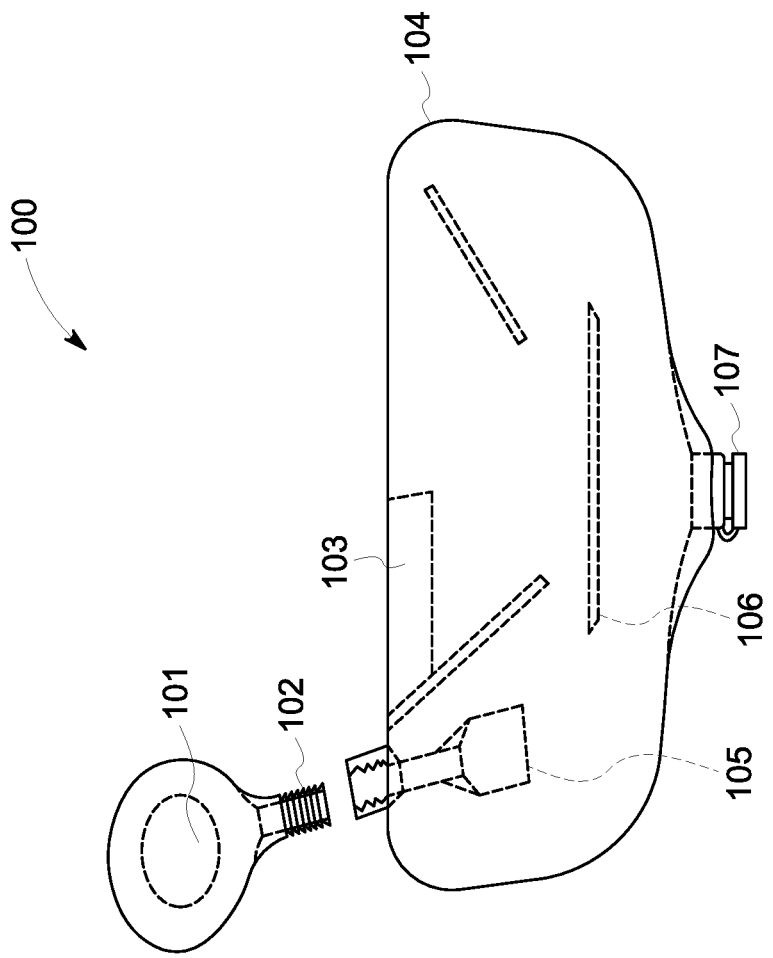
FIG. 1 illustrates a schematic diagram of an ergonomic urine collecting device in accordance to an exemplary embodiment of the invention.

Various embodiments of the present invention will be described in reference to the accompanying drawings. Wherever possible, same or similar reference numerals are used in the drawings and the description to refer to the same or like parts or steps.

The present disclosure has been made with a view towards solving the problem with the prior art described above, and it is an object of the present invention to provide an ergonomic urine collecting device that provides a feeling of passing urine in a natural way, enhances the user comfort and prevents turbulence and bulging of the pouch.

According to an exemplary embodiment of the invention, FIG. 1 refers to a schematic diagram of an ergonomic urine collecting device 100. The ergonomic urine collecting device 100 comprises of a base plate 101, a variable length tube 102, a urine collecting pouch 104, a sensor (not shown), a detachable electronic casing (not shown), and a urine discharge outlet 107. The urine collecting device is ergonomically designed, which easily fits to undergarment and gives a feeling of passing urine in a natural way.

The base plate 101 is configured with an adhesive patch to connect at ostomy site of the patient. The variable length tube 102 is connected to the base plate 101 in connection with a non-return valve 105 to provide a channel to the urine released from the ostomy. The variable length tube is made of medical grade Poly Vinyl Chloride (PVC). The non-return valve 105 is positioned at the end of the variable length tube 102 inside the urine collecting pouch 104 to restrict the backflow of urine. The urine collecting pouch 104 is configured with patterns on inner walls of it to collect urine from the variable length tube 102 without turbulence. In specific, the urine collecting pouch 104 is made of medical grade PVC material which is replaceable and detachable. The patterns on the urine collecting pouch 104 are made using sealing that aids to avoid the turbulence of the urine flow and bulging of the urine collecting pouch 104. The patterns on the urine collecting pouch make the volume-based sensing measurement easy.

The sensor is positioned in a pocket chamber 103 which is arranged on the urine collecting pouch 104 at a threshold level to detect and transmit a signal when the fluid inside reaches a threshold limit. In specific, the sensor includes either a particle sensor or a capacitive sensor using infrared or ultrasound and thereof to detect urine level inside the urine collecting pouch 104. The threshold level for a 400 ml capacity urine collecting pouch is approximately 350 ml. The sensor is placed at a threshold level of 350 to 380 ml of the urine collecting pouch 104. The detachable electronic casing is configured in connection with the sensor to receive the threshold signal and provide haptic feedback to the patient. In specific, the detachable electronic casing comprises a haptic feedback motor, a controller, a power button and a battery, and the controller receives the threshold signal and operates the haptic feedback motor to provide haptic feedback.

The haptic feedback is provided to the patient through a shaft-less motor. The haptic feedback motor is a shaft-less motor comprising either a coin motor or an ERM motor and thereof. The electronic casing is positioned in contact with the patient's body according to their choice and comprises a charging port to recharge the battery inside it. The detachable electronic casing is detached when the urine collecting pouch 104 is replaced and positioned easily after the replacement. The urine discharge outlet 107 connected to the end of the urine collecting pouch 104 is configured with a cap to enable the patient to empty the urine collecting pouch 104 after receiving the haptic feedback or when required. When the urine collecting pouch 104 is filled to a threshold level, the user opens the cap to empty the urine collecting pouch. The urine collecting pouch 104 easily fits inside a custom undergarment of the patient thereby eliminating the change in body image of the user. The variable length tube 102 and the cap are designed to be airtight.

Figure 2A:
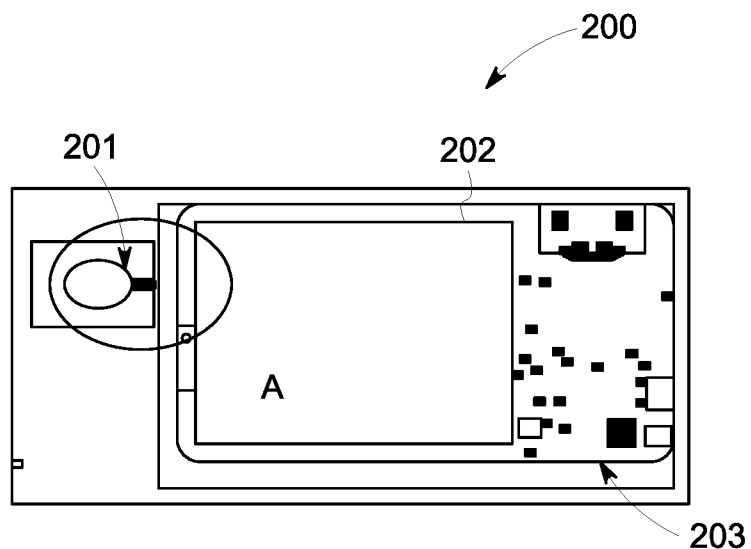
FIG. 2A illustrates a front view of a detachable electronic casing in accordance to an exemplary embodiment of the invention.
Figure 2B:
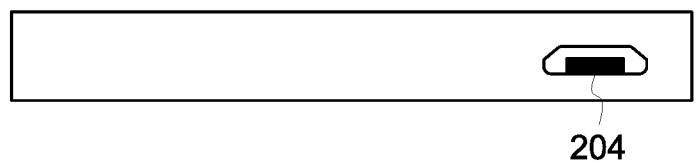
FIG. 2B illustrates a top view of the detachable electronic casing in accordance to an exemplary embodiment of the invention.

According to another exemplary embodiment of the invention, FIG. 2A and FIG. 2B refer to the front view and top view of a detachable electronic casing 200. The detachable electronic casing 200 houses different components including a vibration motor 201 configured to provide vibrations to the user when the urine collecting pouch is filled to a threshold level. The vibrations are provided to the user with 1 second interval for 10 seconds and vibrations repeat after a period of 10 minutes if the user does not empty the bag.

The detachable electronic casing 200 comprises a battery 202, and a PCB 203. The battery 202 utilized is rechargeable and is configured to provide power supply to the vibration motor 201. The battery 202 is provided with a charging port 204 on the top of the detachable electronic casing 200. The detachable electronic casing 200 is charged after detaching from the urostomy patient equipment.

The entire device aids the user to empty the urine collecting pouch after receiving the haptic feedback mimicking the innate human attribute. All the dimensions of the equipment are designed keeping in view the anthropometric data of the human body segments. The urostomy patient equipment is adaptable to any patient irrespective of gender.

Numerous advantages of the present disclosure may be apparent from the discussion above. In accordance with the present disclosure, an ergonomic urine collecting device that provides a natural way of urination. The ergonomic urine collecting device enhances the user comfort and prevents turbulence and bulging of the pouch. The device provides a variable length connector with a one-way valve and the entire equipment fits to the undergarment. The device reduces the risk of infection to the user by utilizing regulated materials to make the urine collection pouch. Further, the ergonomic urine collecting device provides early warning to the user when the contents inside the urine collecting pouch reach a threshold level and aid the user in planning to empty the pouch in time. The proposed device is socially accepted and restores the dignity of the user. The equipment provides haptic feedback to the user when the urine inside the pouch reaches threshold level.

The ergonomic urine collecting device can also be incorporated with an auto mechanized pump with a switch to thereby aid the patient to empty the urine collecting pouch in a stream in standing position. When the user presses the switch, the pump forces the urine out through the cap. The sensor may transmit signal wirelessly to a smartwatch or a smartphone and thereof to alert the user besides vibrations.

It will readily be apparent that numerous modifications and alterations can be made to the processes described in the foregoing examples without departing from the principles underlying the invention, and all such modifications and alterations are intended to be embraced by this application.

I claim:

1. An ergonomic urine collecting device, comprising:
   a base plate configured with an adhesive patch to connect at ostomy site of the patient;
   a variable length tube connected to said base plate in connection with a non-return valve to provide a channel to the urine released from said ostomy;
   a urine collecting pouch configured with patterns on inner walls of it to collect urine from said variable length tube without turbulence;
   a sensor positioned in a pocket chamber which is arranged on said urine collecting pouch at a threshold level to detect and transmit a signal when the fluid inside reaches a threshold limit;
   a detachable electronic casing configured in connection with said sensor to receive the threshold signal and provide a haptic feedback to the patient;
   a urine discharge outlet connected to the end of said urine collecting pouch configured with a cap to enable the patient to empty said urine collecting pouch after receiving said haptic feedback or when required;
   whereby said urine collecting device is ergonomically designed which easily fits inside the undergarment and facilitates natural way of urination to the patient.

2. The ergonomic urine collecting device as recited in claim 1, wherein said non-return valve is positioned at the end of said variable length tube inside said urine collecting pouch to restrict the back flow of urine.

3. The ergonomic urine collecting device as recited in claim 1, wherein said urine collecting pouch is made of medical grade PVC material which is replaceable and detachable.

4. The ergonomic urine collecting device as recited in claim 1, wherein said patterns on said urine collecting pouch are made using sealing that aids to avoid turbulence of the urine flow and bulging of said urine collecting pouch.

5. The ergonomic urine collecting device as recited in claim 1, wherein said sensor includes either a particle sensor or a capacitive sensor or the like to detect urine level inside said urine collecting pouch.

6. The ergonomic urine collecting device as recited in claim 1, wherein said detachable electronic casing comprises a haptic feedback motor, a controller and a battery, and wherein said controller receives the threshold signal and operates the haptic feedback motor to provide haptic feedback at time based intervals.

7. The ergonomic urine collecting device as recited in claim 1, wherein said haptic feedback motor is a shaft-less motor comprising either a coin motor or an ERM motor or the like.

8. The ergonomic urine collecting device as recited in claim 1, wherein said haptic feedback is provided to the patient through a shaft-less motor.

9. The ergonomic urine collecting device as recited in claim 1, wherein said electronic casing is positioned in contact to the patient's body according to their choice and comprises a charging port to recharge the battery inside it.

10. The ergonomic urine collecting device as recited in claim 1, wherein said detachable electronic casing is detached when said urine collecting pouch is replaced and positioned easily after the replacement, wherein said electronic casing has flexibility to re-adjust the location to reduce the phantom vibration.

\* \* \* \* \*